United States Patent [19]

Greer, Jr.

[11] 4,165,649
[45] Aug. 28, 1979

[54] APPARATUS AND METHOD FOR ULTRASONIC INSPECTION OF HIGHLY ATTENUATIVE MATERIALS

[75] Inventor: Amos S. Greer, Jr., San Antonio, Tex.

[73] Assignee: Southwest Research Institute, San Antonio, Tex.

[21] Appl. No.: 549,537

[22] Filed: Feb. 13, 1975

[51] Int. Cl.² .......................................... G01N 29/04
[52] U.S. Cl. ........................................ 73/644; 73/627
[58] Field of Search ........... 73/67.7, 71.5 (U.S. only), 73/617, 624, 627, 644

[56] References Cited

U.S. PATENT DOCUMENTS

| | | | |
|---|---|---|---|
| 2,799,157 | 7/1957 | Pohlman | 73/67.7 |
| 3,485,087 | 12/1969 | Brech | 73/67.7 |
| 3,546,924 | 12/1970 | Nussbaum et al. | 73/67.7 |
| 3,552,191 | 1/1971 | Heseding | 73/67.7 |
| 3,895,685 | 7/1975 | Gillette | 73/67.8 S X |

OTHER PUBLICATIONS

R. C. McMaster, Nondestructive Testing Handbook, sec. 44 pp. 14–19, sec. 45 p. 24, sec. 49 pp. 9–11, The Ronald Press Co., 1959, N.Y.

*Primary Examiner*—Richard C. Queisser
*Assistant Examiner*—John P. Beauchamp
*Attorney, Agent, or Firm*—Hubbard, Thurman, Turner, Tucker & Glaser

[57] ABSTRACT

An ultrasonic inspection system is disclosed which provides for penetration of highly attenuative materials by use of the longitudinal mode of particle vibration. Separate transmitting and receiving transducers, which are electrically isolated, are utilized in the inspection system as are specially designed transducer wedges producing refracted longitudinal ultrasonic waves.

5 Claims, 13 Drawing Figures

APPARATUS AND METHOD FOR ULTRASONIC INSPECTION OF HIGHLY ATTENUATIVE MATERIALS

BACKGROUND OF THE INVENTION

The accelerated growth of the scope and requirements governing non-destructive testing and inspection of materials has prompted a need for improved inspection techniques. As an example, the tightening of requirements governing preservice and inservice examination of nuclear power plants and components has required the advance of non-destructive inspection technology prior to its becoming a useful, practical tool for assuring reactor safety. One of the major problems in nuclear safety is the detection and location of growing flaws such as fatigue cracks in components of the system. Environmental problems such as high temperature and radiation are some of the operational characteristics which must be contended with during the inspection of the reactors. The unique properties of materials utilized in the manufacture of reactor system components also present special problems when attempting to use conventional, non-destructive inspection techniques.

Some coarse-grained austenitic materials, such as static and centrifugally cast stainless steel, are used extensively in the design and construction of nuclear power plant systems and components. Austenitic materials provide metallurgical and economical advantages when used in construction of these systems. However, the material properties of these steels present formidable ultrasonic inspection problems, especially in heavy section vessels and piping components. Characteristics of the material, which contribute to high values of ultrasonic attenuation include grain structure; grain boundary precipitates; grain boundary orientation; and intergranular constituents resulting from preferential or nonuniform cooling rates.

As an example, metallurigical evaluations of the grain structure associated with both static and centrifugally cast stainless steel pipe show the microstructure has a thin layer of equiaxed grains located near the inner diameter of the pipe yielding to a well-defined layer of large columnar grains progressing to the outer diameter of the pipe. This type of grain matrix coupled with a high degree of grain boundary precipitation yields a material structure exhibiting exceptionally high ultrasonic attenuation to a shear mode of particle vibration, and causes the material to exhibit anisotropic behavior from an overall ultrasonic viewpoint.

Material property conditions of this nature, when combined with nonuniform surface conditions normally associated with cast components, generally preclude successful ultrasonic inspection with conventional techniques. Thus, conventional ultrasonic inspection techniques employing either a shear (transverse) mode or longitudinal (compressed) mode of particle vibration have not provided the sensitivity, resolution, reliability, and capability to inspect the types of materials discussed to the degree required by the ASME Boiler and Pressure Vessel Code. In the case of the shear wave the referred to ultrasonic attenuation is the primary reason for lack of positive results. However, failure to successfully inspect such materials with longitudinal ultrasonic waves has been as the result of the failure by the prior art to recognize certain critical factors as described herein.

It is thus an object of this invention to provide highly improved inspection by ultrasonic methods and apparatus of materials such as austenitic steel, whose physical characteristics are generally highly attenuative to ultrasonic waves.

Another object of this invention is to provide ultrasonic inspection apparatus particularly adapted to provide for such improved inspection, and methods of utilizing such apparatus.

Another object of this invention is to provide such apparatus which is relatively simple and inexpensive and can be adapted to use the methods of this invention to inspect objects of different sizes and configurations.

These and other objects of this invention, which will become apparent upon consideration of the appended drawings and claims, and the detailed description of the preferred embodiments of this invention to follow, are accomplished according to this invention by employing a longitudinal wave, i.e., a compressional mode of particle vibration within the material, under controlled and critical conditions to accomplish ultrasonic inspection. As a result of tests conducted by the inventor hereof, this mode of particle vibration has proven to be quite effective when employed under the conditions set out herein in penetrating coarse-grained austenitic steels as well as other types of materials such as ferrous alloyed steel.

In utilizing the longitudinal wave for inspection in accordance with this invention, the process of launching the ultrasonic wave into the material employs several critical techniques. Specially designed wedges, fabricated from plastic material such as Lucite, introduce the longitudinal wave into the material at a prescribed angle depending upon the depth where inspection is to be accomplished or on the orientation of suspected or specific flaws. The system is designed to normally utilize two wedges, one to couple the transmitting transducer which generates the ultrasonic wave and the second to couple the receiving transducer which detects the wave reflected from internal reflectors within the material. By using two independent wedges, the transmitter and receiver networks can be physically isolated to prevent "cross talk" between them, and the wedges may be positioned selectively on the material to be inspected, depending on the specific application.

The wedges also provide for an included angle between the transmitted and reflected wave. This angle is critical and must be adjusted for inspection at various depths in the material as hereinafter explained. Also, the linear separation between the transmitting and receiving wedges is critical, and this distance must be selected to provide proper geometry for the reflected wave to be received by the receiving wedge, but not small enough to allow substantial ultrasonic noise to couple between the two wedges. The transmitting transducer mounted on the wedge is selected to provide the highest efficiency in generating pulsed ultrasonic waves. The sound beam is unfocused; however, normal beam spread provides for a fan-shaped sound beam of essentially equal power distribution within the material.

The ultrasonic energy concentrated within this beam dictates the area in which inspection can be accomplished. In a similar manner, the received transducer mounted upon its wedge is selected to provide the highest efficiency in detecting the wave reflected from internal reflectors. By proper selection of highly efficient transmitting and receiving transducers, and proper selection of wedge angle and separation and proper positioning the ultrasonic energy can be concentrated into the region of interest. The ultrasonic energy is maintained in a longitudinal, or compressional, mode of particle vibration for all examinations, since in contrast to shear waves, the longitudinal waves are influenced less by the material microstructure, thereby providing greater penetration capability.

Special attention is given in the present invention to the design of the Lucite wedge upon which the transducers are mounted. The height of the wedge controlling the distance of the transducer from the material to be inspected is designed to allow dissipation within the wedge of the near field of the wave generated by the transmitting transducer. The near field and far field of the transducer are different, evidenced by a variation in the angular distribution of the wave amplitude as a function of distance from the ultrasonic energy source. The near field is the region in which the wavefront is nonuniform and consists of a number of maxima and minima. The wavefront becomes more uniformly distributed at the point of highest maxima, which is normally termed $Y\dagger$, or the near field limit. Inspections must be performed in the far field of the transducer to achieve uniform results. The Lucite wedge upon which the transmitting transducer is positioned absorbs essentially all of the near field and permits the well-defined far field to be coupled into the material to be inspected. This is basically accomplished by providing a delay that is controlled by the height of the lucite wedge. Although not all of the near field is absorbed or allowed to dissipate, the amount absorbed is adequate to prevent erroneous inspection results caused by near field characteristics and for all practical purposes, the near field is absorbed in the wedge. The wedges are designed to be used with a fluid couplant material such as oil or glycerin to couple the ultrasonic energy from the wedge into the material to be inspected; however, other types of materials such as resilient, elastomeric couplants could be used.

The air space between the transmitting and the receiving wedges prevents the coupling of ultrasonic energy directly from the transmitting wedge into the receiving wedge. The output signal caused by this direct coupling is usually called "cross talk." If the wedges are in contact or if they are positioned closely enough to allow capillary action to draw couplant between them at the surface of the material being inspected, some energy will be coupled directly from one wedge to the other, thereby producing masking signals on the signal display, usually a CRT screen. Although a small amount of energy is coupled between the wedges through the couplant layer along the surface of the component being inspected when no capillary action is present, the level of these signals is low enough to be considered negligible.

In addition to absorbing essentially all of the near field and preventing cross talk, the Lucite wedge provides directional control of the ultrasonic energy and couples the energy into the material to be inspected. It prevents the channeling or focusing of the ultrasonic wave and provides a simple means of directing the ultrasonic beam into the area to be inspected. The size of the crystal used to generate the ultrasonic energy can be selected depending on the application and material thickness. For material thicknesses over two (2) inches, the crystal normally has an area in excess of 0.75 square inches. This large area, combined with the conditioning accomplished by the Lucite wedge, also provides for the ultrasonic wave to be concentrated in an area within the material to be inspected.

The angle of inclination of the Lucite wedges, which controls the angle at which the longitudinal wave enters and exits the material to be inspected, is selected by determining the depth into the material where inspection is to be accomplished. The distance between the transmitting Lucite wedge and the receiving Lucite wedge is also varied along with the angle, so that the reflected wave is detected by the receiving transducer. For example, if an inspection is to be performed at a depth of four (4) inches from the surface where the ultrasonic wave enters the material, the angle of inclusion will be selected and the receiving transducer will be positioned in such a manner that the echo resulting from a flaw in the material will return to a point in the surface of the material covered by the Lucite wedge upon which the receiving transducer is located. Flaws very near the surface will not be detected if the sizes and positions of the transducers and wedges cause the ultrasonic wave to return to the surface in an area outside of the receiving lucite wedge. However, this type of "shallow-depth" flaw may be detected by selecting alternate-sized transmitting and receiving wedges having a different included angle and by positioning the wedges closer to each other than in the former application.

In the drawings, wherein a preferred embodiment of the present invention is illustrated, and where like reference numerals are used thoughout to designate like parts;

Figure 1:
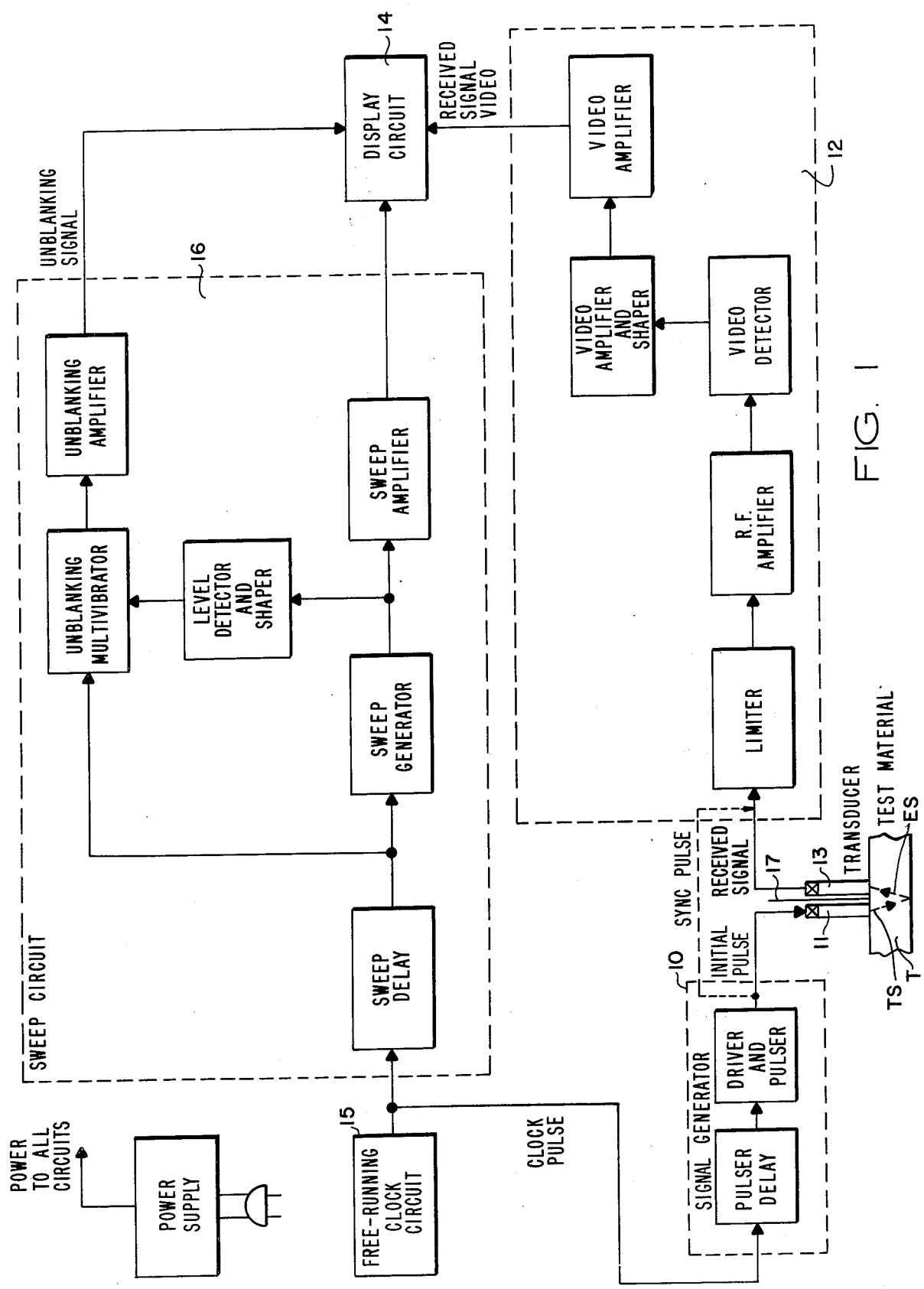
FIG. 1 is a block diagram of the transmitting and receiving electronics used to drive and receive signals from the transducers of the present invention.

FIG. 1 illustrates a preferred electronic circuitry associated with the inspection system and apparatus of the present invention and this circuitry may take many different forms. As illustrated in FIG. 1, the electronics includes a signal generator 10 for generating and applying a pulsed signal to a transmitting transducer 11 for coupling an ultrasonic pulse TS into test material T. Also receiving circuitry 12 is provided for receiving an echo signal ES from a receiving transducer 13 and applying the received signal to a display circuit 14 such as a CRT. In order to synchronize the transmitting and receiving signals, and to synchronize the CRT, a free running clock 15 is provided for providing the clock pulse and synchronizing signals to a sweep circuit 16 which controls the operation of the display circuit 14. The electronics illustrated in FIG. 1 is conventional except that the transducers illustrated are shown as separate transmitting and receiving units with isolation between them illustrated by the line 17 and as more fully explained with respect to the figures to follow.

Figure 2A:
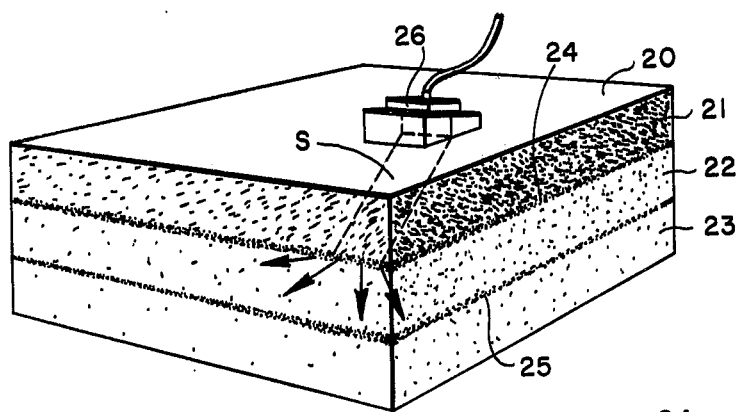
FIGS. 2A and 2B are schematic illustrations of the propagation of an ultrasonic shear wave, through a highly attenuative material, such as austenitic steel.
Figure 2B:
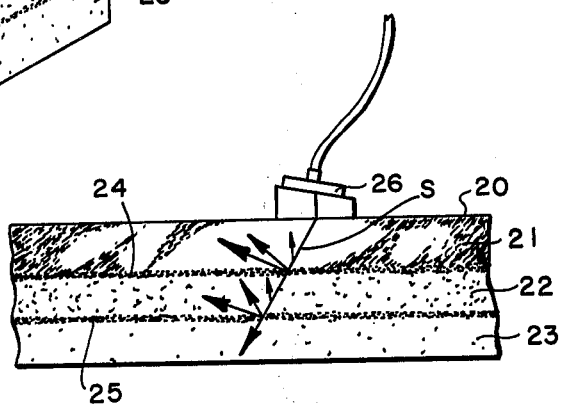

Referring now to FIGS. 2A and 2B, these figures show the cross section of a centrifugally cast stainless steel pipe indicating the grain structure as typically encountered with this type of steel. As illustrated, the grain structure consists of very fine, closed packed grains in the area 23 of test piece 20, progressing into a larger columnar grain structure with more spacing between them in an intermediate section 22, and then into a rather coarse grain structure in the section 21. Distinct grain boundaries 24 and 25 are also illustrated in FIGS. 2A and 2B, and this structure contributes to the ultrasonic attenuation previously discussed, particularly in connection with a shear wave mode of transmission.

FIGS. 2A and 2B also illustrate a transducer 26 operating in a shear mode of particle vibration to provide a shear wave S which is refracted as it propagates through material 20. The shear wave propagates through the material in such a manner that shear stresses are not successfully transferred from one grain matrix to the next, and the particle vibration comprising the shear wave front is in a direction perpendicular to the direction of propagation. In order to propagate a shear wave through a material with little loss of energy, the material must be capable of transferring this shear stress associated with the wave front uniformly with little loss due to attenuation, dispersion, or grain relfections. As illustrated in FIGS. 2A and 2B, the type of material shown, such as austenitic stainless steel, is highly attenuative since the material grain structure serves as a dispersing media and caused frequent small reflections indicated by the arrows from the grain boundaries, each successfully causing a decrease in available energy propagating through the material. In highly attenuative dispering medias such as austenitic steel, this condition is compounded as it is difficult to couple the shear wave from one matrix to the next in the material.

Figure 3A:
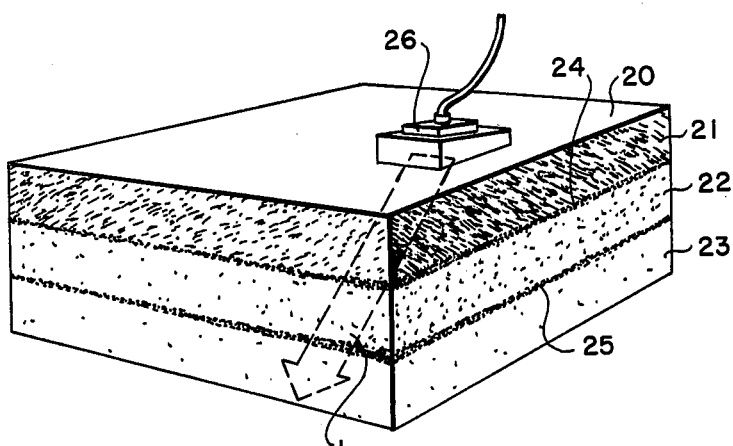
FIGS. 3A and 3B are schematic illustrations of the propagation of an ultrasonic longitudinal wave through such a material.
Figure 3B:
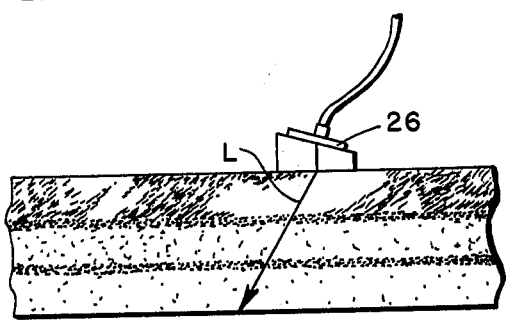

FIGS. 3A and 3B illustrate the same sort of phenomenon as shown in FIGS. 2A and 2B, except that transducer 26 is operated to provide a longitudinal or compressionable mode or particle of vibration as illustrated by the longitudinal wave L propagating through material 20. With a longitudinal wave propagating through this type of material, the particle vibration associated with the wave front is in a direction parallel to the direction of propagation so that compression forces are transferred from each successive grain matrix to the next. Therefore, the grain boundary or grain matrix structure has a less pronounced effect on propagation for the longitudinal type of wave than the shear wave illustrated in FIGS. 2A and 2B. However, in order to successfully utilized the longitudinal or compressional wave for ultrasonic inspection of highly attenuative material, such as illustrated in FIGS. 2A, 2B, 3A and 3B, certain critical factors must be considered as previously discussed in a design of a suitable transducer apparatus for providing the desired inspection and as discussed in detail below.

The material properties previously discussed, which contribute to high attenuation values and cause the material in question to be basically opaque to the propagation of ultrasonic waves are, as noted, related to the metallurgical properties of the material itself. The metallurgical properties can differ according to the base material properties and can be dependent on the welding process joining two pieces of the base material. For example, type 316 or 354 CF8M centrifugally cast stainless steel material exhibits material properties yielding a micro-structure similar to that depicted in FIGS. 2A and 3A. This is the result of preferential cooling rates during the fabrication process. The two distinct and finite bands depicted in the figures result from migration of carbon constituents at the grain boundaries to localized areas of different thermal gradients during the cooling process. The result is a finite metallurgical boundary which acts as a dispersive media to the propagation of ultrasound. The remaining combination of large columnar grain structure and fine equiaxed grain structure results from different grain growth rates experienced during the thermal cooling process. Each of the structures affects the propagation of ultrasonic waves in a distinct manner; for instance, the large columnar grain structure tends to attenuate the ultrasound while at the same time it channels the direction of the sound energy along its grain boundaries. The fine equiaxed grain structure is highly attenuative due to high precipitation rates of the alpha phase at the grain boundaries. It is worthy of note that, during the welding process of materials such as this, the weld material itself exhibits properties directly related to the cooling process it is subjected to and consequently has a large grain structure and high grain boundary precipitation. This structure differs markedly from the adjacent base material grain structure which is, for example, the grain structure exhibited in FIGS. 2A and 3A. The interface between the as-cast weld structure and the base material grain structure produces a metallurgical interface that is difficult to penetrate with ultrasonic waves due to the marked transition in grain boundary constituents, grain growth patterns, and metallurgical phase constituents present.

Although the invention herein disclosed was developed for application to materials very similar to those depicted in FIGS. 2A and 3A, it should be noted that the use of compressional longitudinal energy in the ultrasonic probe is useful in the examination of components fabricated from material exhibiting similar but slightly different metallurgical properties. An example is the category of dissimilar metal weldments found in many nuclear reactors whereby a carbon steel base material is welded to an Inconel or stainless steel spool piece using Inconel weld build-up as a buffering aid in solidfying the welding process. Again, the resulting weld material exhibits an as-cast structure; however, the micro constituents are a combination of Inconel, carbon steel, as stainless steel. The resulting grains structure, although in many cases equiaxed and well formed, exhibits high precipitation content and significantly different acoustic impedance values. As a consequence, the cast weld structure interface with the base material serves as a highly dispersive and reflective media to the propagation of typical transverse or shear stresses. Other types of base material, i.e., Monel, Inconel, Hastalloy and others, although differing somewhat in actual micro constituents, grain orientation, and grain size, produce the same high attenuation values which significantly impede the propagation of shear stresses. The use of the compressional longitudinal energy combined with the inspection techniques as provided by this invention, has been found to be effective for penetrating these types of materials and enabling a non-destructive inspection to be accomplished.

Figure 5:
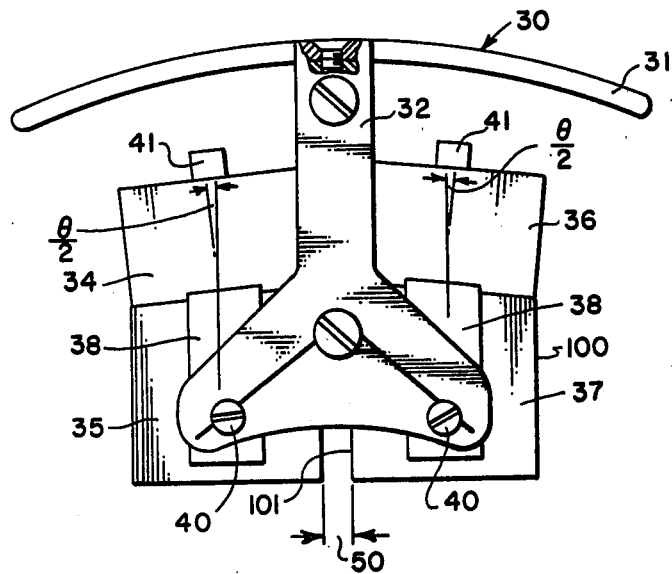
FIG. 5 is a front view in elevation illustrating the preferred form of a probe or mounting assembly for the transducers of the present invention when employed as angle beam transducers.
Figure 6:
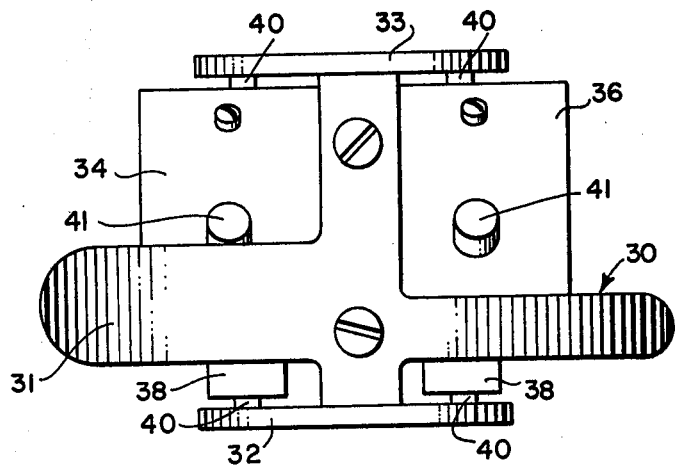
FIG. 6 is a top view of the apparatus of FIG. 5.
Figure 7:
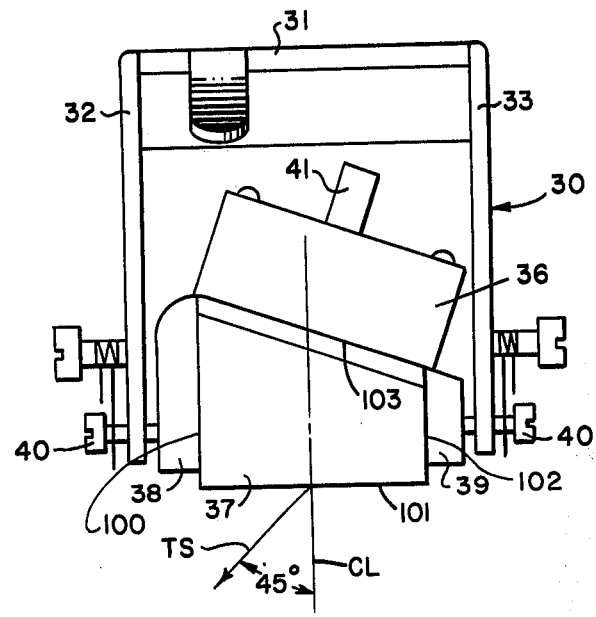
FIG. 7 is a side view of the apparatus of FIG. 5.

FIGS. 5 to 7 illustrate a preferred form of angle beam transducer apparatus utilizing the principles of the present invention to permit successful ultrasonic inspection of a highly attenuative test piece with a longitudinal mode of particle vibration. As illustrated, this apparatus may be provided in the form of an inspection module or probe 30 which can be mounted on a transducer arm or manually used for inspection of a test material, such as pipe. Probe 30 includes a top flange 31 and side flanges 32 and 33 and the transducers of the present invention are pivotally mounted between side flanges 32 and 33 as illustrated. As previously noted, an important feature of the present invention is to provide separate transmitting and receiving transducers which are mechanically and electrically isolated from each other. The embodiment of the probe illustrated in the drawings permits mounting of the separate transmitting and receiving transducers to provide the required isolation and also to permit certain critical relationships required for the present invention between the two transducers. The apparatus illustrated also permits proper positioning and orientation of the transducers on the test material which may, in many instances, be a material having a curved surface, such as pipe.

As illustrated, probe 30 includes a transmitting transducer 34 mounted on a Lucite wedge 35, and a receiving transducer 36 mounted on a lucite wedge 37. Wedges 35 and 37 are, in turn, mounted by spacers 38 and 39, and screws 40 (see FIG. 7) between side plates 32 and 33 so that each of the transducers is free to rotate to comply with the contour of the material to be inspected by pivoting about the screws 40. Also, each of the transducers includes a signal connector 41 for connection with the electronics of FIG. 1.

As previously discussed, a critical included angle $\theta$ is provided between the receiving and transmitting transducers. In FIG. 5, this angle is illustrated as including the angles $\theta/2$ each of which is the angle from the perpendicular, in the direction toward the other transducer, that each transducer is mounted on its respective wedge. As noted, the angle $\theta$ may range from about a minimum of 3° to a maximum of about 10°, depending on the thickness of the material being inspected and the size of the transducers, and the specific design of the Lucite wedges on which the ultrasonic transducers are mounted in the angle beam inspection module illustrated provides a nominal five to ten degrees included angle between the tow units. This angulation of the transducers serves the purpose of angularly directing the ultrasonic energy transmitted through the Lucite wedge into the material to be inspected in a manner which will provide optimum reflection characteristics if the ultrasonic energy impinges on a reflector.

The included angle assists in defining a closure envelope of essentially uniform ultrasonic intensity for a particular depth within the material to be inspected. Increasing or decreasing the included angle will cause a concurrent increase or decrease in the effective depth at which the signal is applied. Also, an increase in the included angle will render the examination only partially effective. This is because the transmitted ultrasonic energy will be angled such that the reflections from discontinuities at depths within the material greater than one-fourth ($\frac{1}{4}$) the total thickness may completely bypass the receiving transducer. For example, an included angle of 10° for inspection of a steel component 3-$\frac{1}{2}$" thick produces a sound beam envelope providing uniform intensity throughout the test piece. An increase in the included angle to 13° yields a uniformly distributed acoustic envelope only to a depth of 1.8". Similar results will occur with a decrease in included angle to 3° or less. However, in this case the transmitted ultrasonic energy is transmitted very nearly perpendicularly into the test piece, thereby decreasing the efficiency of the receiver transducer pick-up capability. As such, the included angle remains a critical item and it can be adjusted to realize more efficient inspection capability depending on thickness of the material inspected.

Figure 10:
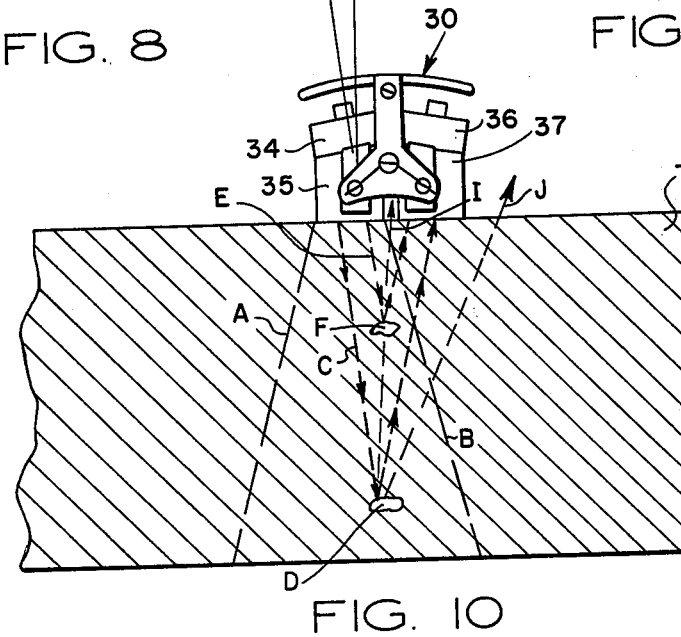
FIG. 10 illustrates the transducer assembly of FIG. 5 mounted on a test piece to show the relationship between the transmitted and received signals.

The criticality of the included angle is illustrated by FIG. 10 where ultrasonic sound waves are propagated in test piece T from transmitting transducer 34 within the band represented by the lines A-B along line C to a relatively deep flaw D and line E to a relatively shallow flaw F. With an included angle $\theta$ within the specified critical range (3°-10°) echo signals G and H respectively are received from flaws D and F by receiving transducer 36. However, if the angle $\theta$ is too small, then the maximum echo signal can be received within the space 50 between the transducers as represented by line I, whereas if angle $\theta$ is too large, the maximum echo signal may return outside the inspection module as represented by line J. Because of the attenuation of the sound waves in the materials referred to, it is important that as close to the maximum strength echo signal to be received by transducer 36.

Also, as previously noted, the spacing, represented by the numeral 50 in FIG. 5, between the transducers and their wedges is critical because the wedges must be properly placed to allow transmission of acoustic energy and permit detection of reflected energy with a minimum of coupling noise. Laboratory tests have indicated that with the one-inch by one-inch transducer referred to, that the spacing between the wedges may be between 0.03 and 0.15 inches. If the wedges are spaced below this minimum value (taking into account the critical angle between them) acoustic energy will be directly coupled through the coupling material from the transmitting wedge into the receiving wedge, thereby causing extraneous signals that affect the signal noise ratio. For example, a decrease in Lucite wedge spacing from 0.030" to 0.010" increases cross talk between the wedges by a factor of three. Since the Lucite wedges supporting the ultrasonic transducers are individually pivoted, very small spacing between the wedges restricts the pivotal movement of the wedges and restricts the device to application on a much larger diameter pipe. Greater spacing distances between the Lucite wedges allows more freedom in the pivoting characteristics of the device and thereby allows inspection of pipes with much smaller diameter. However, spacing of wedges in excess of the recommended maximum value may cause the wedges to be inefficient in receiving and processing reflected signals from the test material since the receiving transducer may be positioned beyond the point where it would receive the maximum strength echo signal.

In addition, the wedge height is critical and should generally be within a range for both the straight beam and angle beam transducers of about 15/16 to about 1-5/16 inches on the outside front leading edge of the wedge (labeled 100 in FIG. 5), and about 1 to about 1-⅜ inches on the inside front leading edge (labeled 101 in FIG. 5). Also, the wedge height for the angle beam transducer should generally be within a range of about 5/16 to about 11/16 inches on the rear outside trailing edge (labeled 102 in FIG. 7) and about 7/16 to about 13/16 inches on the rear inside trailing edge (not shown in the drawings). An optimum figure for these measurements has been found to be about 1-⅛ inches for edge 100, about 1-3/16 inches for edge 101, and about ½ inch for edge 102, and about ⅝ inch for the rear inside trailing edge of the wedge. These measurements are critical in that they must be large enough to allow the near field of the sound beam to be partially dissipated within the wedge material, but not so large as to allow the beam spread of the transducer to provide internal wedge reflections which are detrimental to inspection.

The height of the Lucite wedges has a direct bearing on the amount or percentage of the near field components of the ultrasonic beam which can be absorbed prior to entry of the ultrasonic energy into the test piece. For instance, when inspecting a steel component, a Lucite wedge of very minimal height, such as ¼", will absorb only 30% of the near field components in the ultrasonic beam generated by a one (1) inch diameter transducer. Therefore, the effective inspection area within the test piece is limited, since the additional 70% of the near field properties must be absorbed in the test piece itself. Adjustment of the height of the Lucite wedge to the proper value depending on the type of material to be inspected, that is, steel, aluminum, Inconel, etc., will provide the capability for absorbing a substantial amount of the near field components, thereby providing a uniform field transmission within the test piece. It is obvious that the physical height of the Lucite wedges can and should be adjusted depending on the material to be inspected and the size and frequency of the transducers used.

Figure 4A:
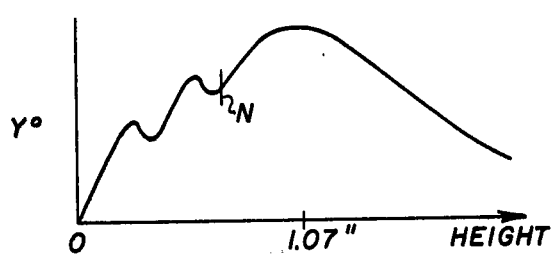
FIGS. 4A and 4B are graphs illustrating maximum and minimum of far field transmission of a longitudinal wave from the transducers of the present invention.
Figure 4B:
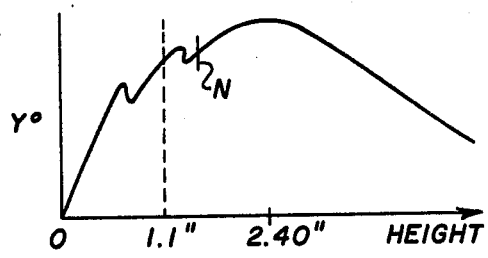

FIGS. 4A and 4B illustrate the absorbing of the near field transmission in a steel member (FIG. 4A) or a Lucite member (FIG. 4B). The line N represents the approximate near field limit in each case and as shown in FIG. 4B a Lucite wedge height of approximately 1.1" will absorb a substantial portion of the near field transmission, and at this point the beam has not spread so to provide extraneous reflections.

The angle beam inspection module shown in FIGS. 5–7 is designed to provide nominal 45° refracted longitudinal energy into a steel test piece, and the mounting of the transducers on the Lucite wedges in order to accomplish this is illustrated in FIG. 7. Development tests have indicated that inspection angles nominally between 40° and 50° provide the best inspection results. This is also due to expected orientation of reflectors and transmission characteristics of typical steel test components. The 45° refracted longitudinal energy is centered within the range of high power transmission efficiency for introduction of compressional ultrasonic energy across an interface; in our case, for example, from the Lucite wedge into the steel piece. Developmental tests have proven that the angle of incidence may be increased or decreased from 45°, but the most effective inspection occurs nominally at an angle of 45°.

Figure 8:
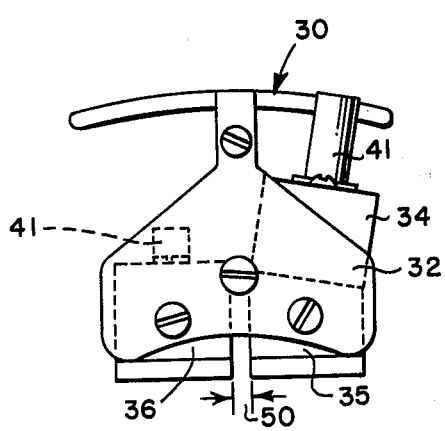
FIG. 8 is a view in elevation illustrating the preferred form of mounting the assembly for the straight beam transducer assembly of this invention, showing the transducers thereon.
Figure 9:
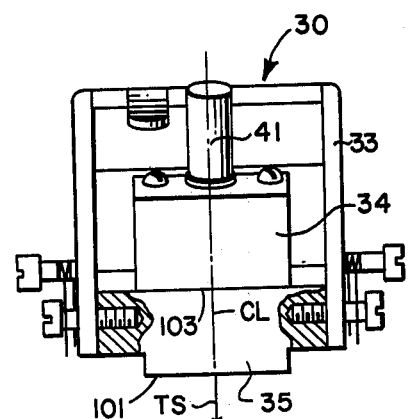
FIG. 9 is a side view with a partial cutaway taken illustrating further the apparatus of FIG. 8.

It is also possible to employ a straight-beam inspection module wherein a longitudinal wave is generated such that the angle of refraction is 0°. Such a module is shown in FIGS. 8 and 9. In this specific module, the Lucite wedge is not needed with the receiving transducer; however, the inspection module is otherwise similar to that shown in FIGS. 5–7 except that the position of the receiving transducer 36 and transmitting transducers are reversed. Also, in order to obtain the straight beam of inspection, the faces of the transducer 34 and Lucite wedge 35 (represented by lines 101 and 103 in FIG. 9) are substantially parallel, whereas they are at a substantial angle with respect to each other is shown by reference numerals 101 and 103 in FIG. 7, for the angle beam inspection mode. Since the angle of refraction is 0° between beam TS and the centerline represented by reference CL (as opposed to 45° in FIG. 7), the face of the receiving transducer 36 can be placed directly upon the surface of the material. The Lucite wedge must be used with the transmitting transducer since it still absorbs the near field, reduces the cross talk, and isolates the system (as described in the explanation of the angle-beam inspection module).

Both types inspection modules illustrated produce longitudinal ultrasonic waves for performance of inspections. In both the angle-beam and straight-beam inspection modules, the design maintains the same included angle of approximately 3° to 10°. The linear separation of the plastic wedges in the angle-beam inspection module also corresponds to the linear separation between the transmitting wedge and the receiving transducer in the straight-beam inspection module.

Thus, an inspection system has been illustrated and described which permits effective ultrasonic inspection of highly attenuative materials such as austenitic stainless steel for various applications.

From the foregoing, it will be seen that this invention is one well adapted to attain all of the ends and objects hereinabove set forth, together with other advantages which are obvious and which are inherent to the apparatus.

As many possible embodiments may be made of the invention without departing from the scope thereof, it is to be understood that all matter herein set forth or shown in the accompanying drawings is to be interpreted as illustrative and not in a limiting sense.

What is claimed is:

1. An inspection module for ultrasonically inspecting materials that are highly attenuative to the propagation of ultrasonic waves, comprising, in combination:

a module frame for supporting the components of said inspection module;

an absorption medium pivotally mounted on said frame and including a first face adapted to be placed at least adjacent the object to be inspected and a second face, said absorption medium having sufficient thickness between said first and said second face to absorb a substantial part of the near-field of any transmitted ultrasonic waves without appreciably interfering with the transmission of the far-field of such waves;

a transmitting transducer mounted on said second face for generating longitudinal ultrasonic waves;

a receiving transducer for receiving ultrasonic waves from said object to be inspected, and spaced a relatively small but effective distance from said transmitting transducer to receive desired ultrasonic signals with a relatively small amount of cross-talk between said transducers, the transmitting transducer being mounted on said second face and positioned in one direction on said face with respect to said receiving transducer to have a small but effective included angle with said receiving transducer to provide for substantially uniform inspection in said highly attentuative material throughout a generally fan shaped envelope of inspection; and a second absorption medium pivotally mounted on said frame and having a first face adapted to be placed at least adjacent the object to be inspected and a second face, and wherein said receiving transducer is mounted on said second face, the second faces of each absorption medium having a first angle in one direction with respect to said object to be inspected to provide said included angle, and a second angle in a direction perpendicular to said first direction to provide an angle of refraction for the longitudinal inspection beam of substantially greater than 0°.

2. The inspection module of claim 1 wherein said included angle is from about 3° to about 10°.

3. The inspection module of claim 1 wherein said angle of refraction is about 40° to 50°.

4. The inspection module of claim 2 wherein said angle of refraction is about 40° to 50°.

5. The inspection module of claim 1 wherein said included angle is from about 3° to about 10°.